(12) United States Patent
Hosoe et al.

(10) Patent No.: US 10,751,251 B2
(45) Date of Patent: Aug. 25, 2020

(54) MEDICAL PREPARATION DIVIDING UNIT AND MEDICAL PREPARATION DIVIDING METHOD

(71) Applicant: TERUMO KABUSHIKI KAISHA, Tokyo (JP)

(72) Inventors: Kaoru Hosoe, Tokyo (JP); Koudai Nagata, Tokyo (JP)

(73) Assignee: Terumo Kabushiki Kaisha, Tokyo (JP)

( * ) Notice: Subject to any disclaimer, the term of this patent is extended or adjusted under 35 U.S.C. 154(b) by 227 days.

(21) Appl. No.: 15/709,760

(22) Filed: Sep. 20, 2017

(65) Prior Publication Data

US 2018/0078454 A1   Mar. 22, 2018

(30) Foreign Application Priority Data

Sep. 20, 2016   (JP) .................. 2016-182879

(51) Int. Cl.
| | |
|---|---|
| *A61J 1/10* | (2006.01) |
| *A61M 1/00* | (2006.01) |
| *A61B 5/15* | (2006.01) |
| *A61J 1/20* | (2006.01) |

(Continued)

(52) U.S. Cl.
CPC ........... *A61J 1/10* (2013.01); *A61B 5/150366* (2013.01); *A61J 1/16* (2013.01); *A61J 1/20* (2013.01); *A61M 1/0021* (2013.01); *A61M 1/0209* (2013.01); *A61M 1/0277* (2014.02); *A61M 2209/082* (2013.01); *A61M 2240/00* (2013.01)

(58) Field of Classification Search
CPC .... A61M 1/0209; A61M 2240/00; A61J 1/10; A61J 1/16; A61J 1/20
See application file for complete search history.

(56) References Cited

U.S. PATENT DOCUMENTS

| | | |
|---|---|---|
| 3,187,750 A | 6/1965 | Tenczar, Jr. |
| 4,994,039 A | 2/1991 | Mattson |
| 5,356,373 A | 10/1994 | Dracker |

(Continued)

FOREIGN PATENT DOCUMENTS

| | | |
|---|---|---|
| CN | 201192459 Y | 2/2009 |
| CN | 101953750 A | 1/2011 |

(Continued)

OTHER PUBLICATIONS

Espacenet Translation of Kiprov, Hajnal (WO2015/149098 A1), published Oct. 5, 2015. Translation retrieved Aug. 5, 2019 (Year: 2015).*

(Continued)

*Primary Examiner* — Elizabeth Insler
(74) *Attorney, Agent, or Firm* — Terumo BCT, Inc IP Law Dept (57) ABSTRACT

A medical preparation dividing method is dividing a medical preparation stored in a storage member into a plurality of division bags by gravitational force through a primary tube, a branch portion, and a plurality of branch tubes. A medical preparation dividing unit has a curved portion formed in another end side of the primary tube, an inlet of the branch portion arranged above the curved portion, and outlets of the branch portion arranged above the inlet, in a state where the plurality of division bags is held with a holding tool.

6 Claims, 9 Drawing Sheets

(51) Int. Cl.
  *A61M 1/02*  (2006.01)
  *A61J 1/16*  (2006.01)

(56) References Cited

U.S. PATENT DOCUMENTS

| 2005/0051486 A1* | 3/2005 | Zuk, Jr. | A61M 1/0209 |
| | | | 210/645 |
| 2012/0171658 A1 | 7/2012 | Bein et al. | |
| 2015/0005734 A1* | 1/2015 | Inoue | A61J 1/14 |
| | | | 604/500 |

FOREIGN PATENT DOCUMENTS

| WO | 2015149098 A1 | 10/2015 | | |
| WO | WO-2015149098 A1 * | 10/2015 | .......... | A61M 1/0001 |

OTHER PUBLICATIONS

European Searching Authority; Annex to European Search Report, EP 17 19 1827; dated Feb. 1, 2018, 11 pages.
Fujishima, Mitsuhiro et al. "Transfusion of Divided Red Blood Cells During Neonatal Period", Division of Blood Transfusion, Japanese Journal of Transfusion Medicine, vol. 49, No. 3 St. Mary's Hospital, Nov. 29, 2002, pp. 426-431.
Fujishima, Mitsuhiro et al. "Transfusion of Divided Red Blood Cells During Neonatal Period", Division of Blood Transfusion, St. Mary's Hospital, Nov. 29, 2002, 9 pages. (English Translation).

\* cited by examiner

MEDICAL PREPARATION DIVIDING UNIT AND MEDICAL PREPARATION DIVIDING METHOD

RELATED APPLICATION

This application claims the benefit of priority from Japanese Application JP2016-182879 filed Sep. 20, 2016.

BACKGROUND

Technical Field

The present invention relates to a medical preparation dividing unit and a medical preparation dividing method for dividing a medical preparation stored in a storage member into a plurality of division bags by difference in height.

Related Art

To effectively use a blood preparation, division of the blood preparation is performed in each hospital in a case of transfusing blood into a newborn infant or an immature infant, where the volume of single blood transfusion is small. The division of the blood preparation is performed by absorbing the blood preparation in a blood sampling bag with a syringe. However, this method has a risk of contamination of the blood preparation (for example, see Mitsuhiro Fujishima and three others, 2003, "Transfusion of Divided Red Blood Cells During Neonatal Period", Journal of the Japan Society of Blood Transfusion, Vol. 49, No. 3, pp. 426-431).

Further, Mitsuhiro Fujishima and three others, 2003, "Transfusion of Divided Red Blood Cells During Neonatal Period", Journal of the Japan Society of Blood Transfusion, Vol. 49, No. 3, pp. 426-431 describes a method of connecting a blood sampling bag and a plurality of division bags through a branch tube in an aseptic condition, and transferring a blood preparation in the blood sampling bag into the division bags.

SUMMARY

By way of example, in a case of transferring a medical preparation such as a blood component in a blood sampling bag (storage member) into a plurality of division bags while causing the medical preparation to flow by gravity from above to below in a branch tube, the medical preparation is nonuniformly divided into the plurality of division bags due to nonuniformity of resistance in the branch tube provided to the medical preparation at the time of gravity flow. Therefore, to divide the medical preparation into the plurality of division bags in an approximately uniform manner, the medical preparation in the division bags needs to be measured and adjusted, and the work is difficult.

The present invention has been made in view of such a problem, and an objective is to provide a medical preparation dividing unit and a medical preparation dividing method that enable approximately uniform division of a medical preparation in a storage member into a plurality of division bags by simple and easy work.

To achieve the objective, a medical preparation dividing unit according to the present invention is a medical preparation dividing unit for dividing a medical preparation stored in a storage member into a plurality of division bags by gravity flow, the medical preparation dividing unit including a primary tube having one end to which the storage member is connectable, a branch portion provided to the other end of the primary tube, a plurality of branch tubes having one ends connected to the branch portion, the plurality of division bags having inlets to which the other ends of the branch tubes are connected, and formed into the same shape and the same size as one another, and a holding tool for holding the plurality of division bags with the inlets facing downward, below the storage member, and for holding the plurality of inlets at the same height position above the branch portion, wherein a curved portion is formed in the primary tube on the other end side, an inlet of the branch portion is arranged above the curved portion, and outlets of the branch portion are arranged above the inlet of the branch portion, in a state where the plurality of division bags is held with the holding tool.

According to the configuration, when the medical preparation in the storage member is positioned above the primary tube in a state where the plurality of division bags is held with the holding tool, the medical preparation introduced from the primary tube flows into the plurality of branch tubes while pushing up the air in the branch portion. With the configuration, in the branch portion and the branch tubes, the medical preparation flows against the force of gravity in an opposite direction to a proceeding direction of flow of the fluid (medical preparation). Therefore, flow separation in the branch portion and the branch tubes is suppressed, and influence of nonuniformity of a tube shape on the branch portion and the branch tubes can be reduced. Therefore, as a result, the medical preparation can be approximately uniformly transferred to the branch tubes. Then, the medical preparations through the branch tubes are approximately uniformly transferred to the plurality of division bags having the inlets having the same shape and the same size as one another and held at the same height. Therefore, the medical preparation in the storage member can be approximately uniformly divided into the plurality of division bags by simple and easy work.

The medical preparation dividing unit may further include a shape holding tool that holds the other end side of the primary tube in a curved shape so that the medical preparation is introduced through the primary tube into the branch portion from below.

According to the configuration, the medical preparation in the branch portion can be reliably brought to flow upward.

In the medical preparation dividing unit, flow path volumes of the plurality of branch tubes may be approximately the same as one another.

According to the configuration, the medical preparation can be further uniformly transferred to the plurality of division bags.

In the medical preparation dividing unit, central lines of the plurality of outlets of the branch portion may be positioned on the same circumference around a central line of the inlet of the branch portion.

According to the configuration, the medical preparation introduced into the inlet of the branch portion can be uniformly transferred to the branch tubes with a simple configuration.

In the medical preparation dividing unit, the holding tool may include a connection portion that connects the plurality of division bags with one another, and a mount portion provided to the connection portion and detachably mountable to the primary tube.

According to the configuration, the inlets of the plurality of division bags can be easily held at approximately the same height by mounting the mount portion to the primary tube.

In the medical preparation dividing unit, a breakable portion may be formed in the connection portion so that the plurality of division bags is separable from one another.

According to the configuration, the division bags can be separated from one another by breaking the breakable portion of the connection portion after the medical preparation in the storage member is divided into the plurality of division bags.

The medical preparation dividing unit may further include a clamp capable of blocking or opening the primary tube.

According to the configuration, the clamp is opened and the medical preparation in the storage member can be divided into the plurality of division bags, after the plurality of division bags is held with the holding tool.

A medical preparation dividing method of the present invention is a medical preparation dividing method of dividing a medical preparation stored in a storage member into a plurality of division bags through a primary tube, a branch portion, and a plurality of branch tubes, the method including a connection process of connecting the storage member to one end of the primary tube, a holding process of holding, with a holding tool, the plurality of division bags with inlets facing downward, below the storage member and holding the inlets of the plurality of bags at the same height above the branch portion, the plurality of division bags being formed into the same shape and the same size as one another, and a transfer process of transferring the medical preparation to the plurality of division bags through the branch portion and the branch tubes, by flowing the medical preparation by gravitational force from the storage member to the primary tube after the holding process, wherein, in the transfer process, the medical preparation is transferred to the branch portion through another end side that is curved, of the primary tube, flows upward in the branch portion, and is transferred to the plurality of division bags through the plurality of branch tubes.

According to the method, the medical preparation in the storage member can be approximately uniformly divided into the plurality of division bags by simple and easy work.

In the medical preparation dividing method, a shape holding process of holding the other end side of the primary tube into a curved shape with a shape holding tool may be performed before the transfer process so that the medical preparation is introduced through the primary tube into the branch portion from below.

According to the configuration, in the transfer process, the medical preparation in the branch portion can be reliably brought to flow upward.

In the medical preparation dividing method, a residual amount transfer process of causing the medical preparation in the primary tube to flow downward to the division bags through the branch portion and the branch tubes may be performed by canceling the holding of the plurality of division bags with the holding tool after the transfer process.

According to the method, the total amount of the medical preparation in the storage member can be divided into the plurality of division bags.

In the medical preparation dividing method, the holding tool may include a connection portion that connects the plurality of division bags with one another, and a separation process of separating the plurality of division bags from one another may be performed by cutting the connection portion after the residual amount transfer process.

According to the method, a plurality of division bags can be individually stored and used.

According to the present invention, when a medical preparation in a storage member is caused to flow by gravity into a primary tube, the medical preparation introduced through the primary tube into an introduction portion of a branch connector flows into a plurality of branch ports while pushing up the air in the branch connector from below. Therefore, the medical preparation in the storage member can be approximately uniformly divided into a plurality of division bags by simple and easy work.

DETAILED DESCRIPTION

Hereinafter, favorable embodiments about a medical preparation dividing unit and a medical preparation dividing method according to the present invention will be described with reference to the appended drawings.

Figure 1:
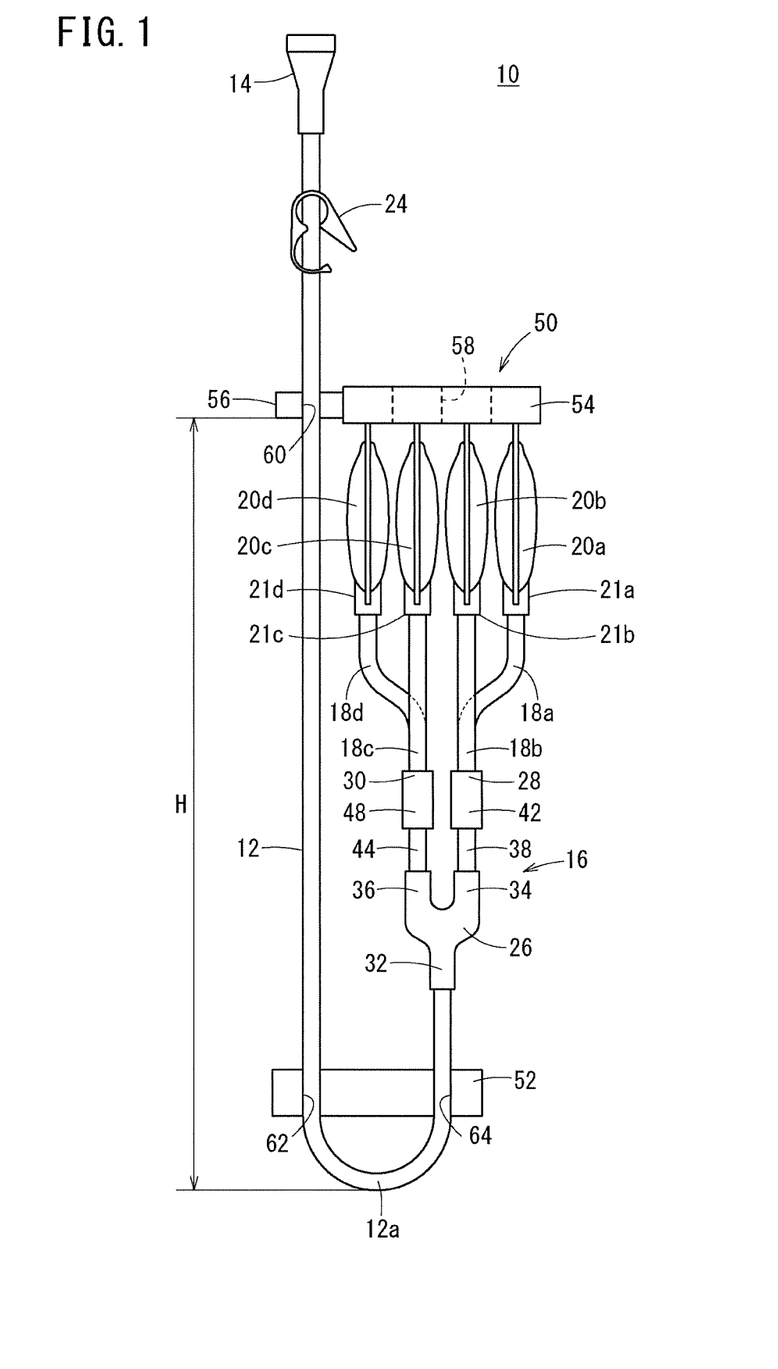
FIG. 1 is a schematic front view of a medical preparation dividing unit according to an embodiment of the present invention.
Figure 2:
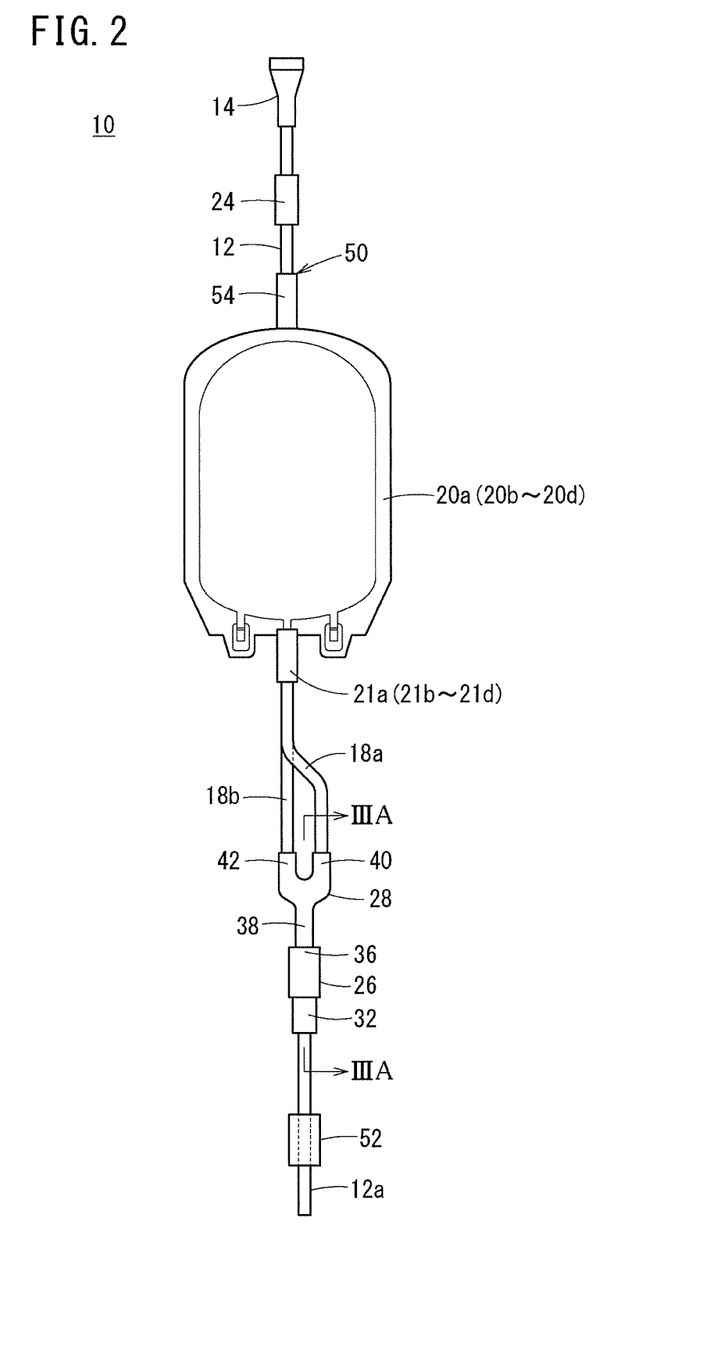
FIG. 2 is a schematic side view of the medical preparation dividing unit in FIG. 1.

As illustrated in FIGS. 1 and 2, a medical preparation dividing unit 10 according to an embodiment of the present invention divides a medical preparation stored in a storage bag 100 (storage member) into a plurality of division bags 20*a* to 20*d* in an approximately uniform manner by gravitation. As the medical preparation, a liquid preparation such as a blood preparation or a cell preparation is used, for example. Examples of the blood preparation include whole blood, packed red blood cells blood plasma, blood platelet, platelet-rich plasma, and platelet poor plasma.

For example, the medical preparation dividing unit 10 can be used to divide blood (the medical preparation) stored in a blood sampling bag (the storage bag 100) into the plurality of division bags 20*a* to 20*d* in an approximately uniform manner, as in a case of transfusing blood into a newborn infant or an immature infant, where the volume of single blood transfusion is small.

The medical preparation dividing unit 10 of the present embodiment is used to divide the medical preparation in one storage bag 100 (storage member) (see FIG. 4) into the four division bags 20*a* to 20*d*. Note that the medical preparation dividing unit 10 may be used to divide the medical preparation in one storage bag 100 into two, three, or five or more division bags 20a to 20d. Further, the medical preparation dividing unit 10 may be used to divide the medical preparation in two or more storage bags 100 into three or more (a larger number than the number of the storage bags 100) division bags 20a to 20d.

The medical preparation dividing unit 10 includes a long primary tube 12, a valve member 14 provided to one end of the primary tube 12, a branch portion 16 provided to the other end of the primary tube 12, a plurality of branch tubes 18a to 18d having one ends connected to the branch portion 16, and the plurality of division bags 20a to 20d having inlets 21a to 21d connected with the other ends of the branch tubes 18a to 18d.

The primary tube 12 is a transparent and flexible resin-made tube. The branch tubes 18a to 18d are similar to the primary tube 12. The valve member 14 is an air vent for adjusting an internal pressure in performing high pressure steam sterilization (autoclave sterilization) of the medical preparation dividing unit 10, for example. The valve member 14 may be omitted in a case of applying ethylene oxide gas sterilization (EOG sterilization) or radiation sterilization (gamma sterilization) to the medical preparation dividing unit 10. A clamp 24 that blocks or opens the primary tube 12 is provided to one end side (a middle portion) of the primary tube 12.

Figures 3A, 3B:
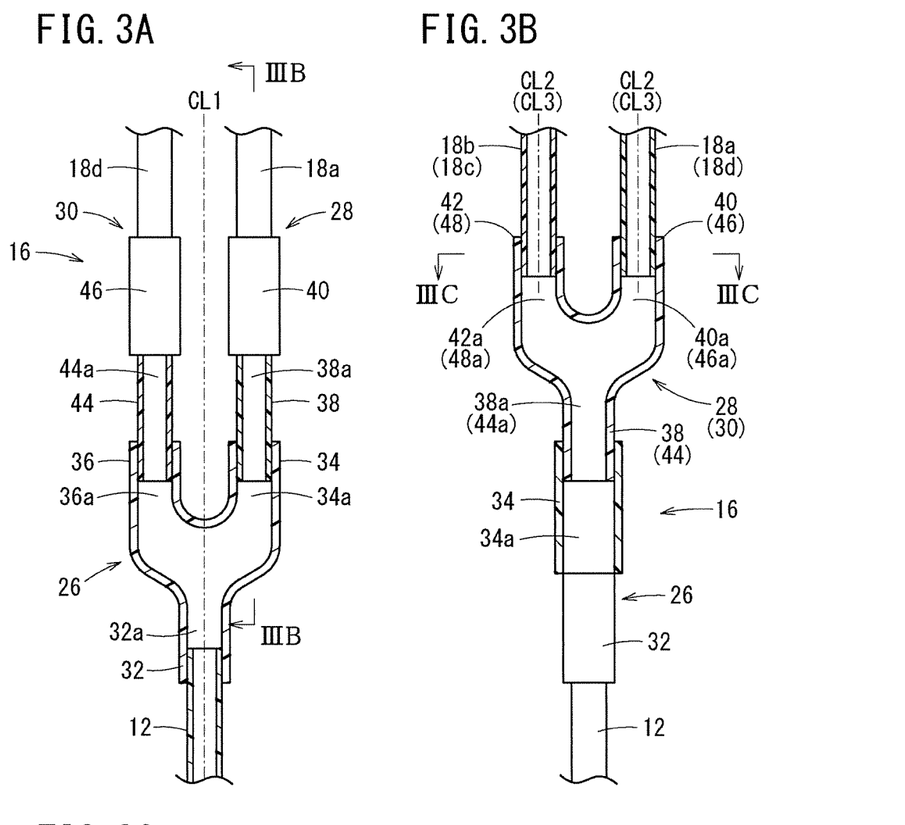
FIG. 3A is a sectional view along a IIIA-IIIA line in FIG. 2.
FIG. 3B is a sectional view along a IIIB-IIIB line in FIG. 3A.

As illustrated in FIGS. 3A and 3B, the branch portion 16 includes primary to third branch portions 26, 28, and 30. Each of the primary to third branch portions 26, 28, and 30 is formed as a Y connector. In other words, the primary to third branch portions 26, 28, and 30 are formed into the same shape and the same size as one another, and a combination of these members constitutes the branch portion 16.

The primary branch portion 26 includes a primary leg portion 32 and two primary arm portions 34 and 36 extending in a bifurcated manner from the primary leg portion 32. A primary introduction portion 32a (an inlet of the branch portion 16), in which the other end portion of the primary tube 12 is provided, is formed in the primary leg portion 32.

A primary branch port 34a communicating with the primary introduction portion 32a is formed in the primary arm portion 34. The primary arm portion 36 formed similarly to the primary arm portion 34, and a primary branch port 36a communicating with the primary introduction portion 32a is formed in the primary arm portion 36. The primary branch portion 26 is line-symmetrically formed with respect to a central line CL1 of the primary introduction portion 32a, as an axis of symmetry.

The second branch portion 28 is formed similarly to the primary branch portion 26, and includes a second leg portion 38 provided in the primary branch port 34a and two second arm portions 40 and 42 extending in a bifurcated manner from the second leg portion 38. A second introduction port 38a communicating with the primary branch port 34a is formed in the second leg portion 38.

A second branch port 40a communicating with the second introduction port 38a is formed in the second arm portion 40. The second branch port 40a is provided with one end portion of the branch tube 18a. The second arm portion 42 is formed similarly to the second arm portion 40, and a second branch port 42a communicating with the second introduction port 38a is formed in the second arm portion 42. The second branch port 42a is provided with one end portion of the branch tube 18b. That is, these second branch ports 40a and 42a function as outlets of the branch portion 16. An arranging direction of the second arm portions 40 and 42 is perpendicular to an arranging direction of the primary arm portions 34 and 36.

The third branch portion 30 is formed similarly to the primary branch portion 26, and includes a third leg portion 44 provided in the primary branch port 36a and two third arm portions 46 and 48 extending in a bifurcated manner from the third leg portion 44. A third introduction port 44a communicating with the primary branch port 36a is formed in the third leg portion 44.

A third branch port 46a communicating with the third introduction port 49a is formed in the third arm portion 46. The third branch port 46a is provided with one end portion of the branch tube 18d. The third arm portion 48 formed similarly to the third arm portion 46, and a third branch port 48a communicating with the third introduction port 44a is formed in the third arm portion 48. The third branch port 48a is provided with one end portion of the branch tube 18c. That is, these third branch ports 46a and 48a function as outlets of the branch portion 16. An arranging direction of the third arm portions 46 and 48 is perpendicular to an arranging direction of the primary arm portions 34 and 36. That is, the arranging direction of the third arm portions 46 and 48 is the same as the arranging direction of the second arm portions 40 and 42.

Figure 3C:
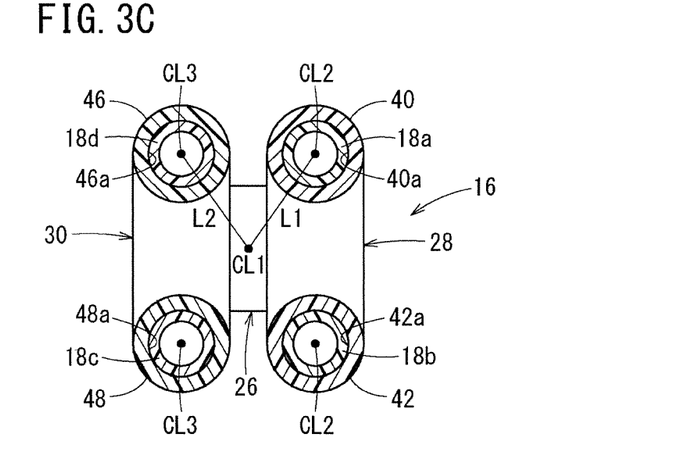
FIG. 3C is a sectional view along a IIIC-IIIC line in FIG. 3B.

As illustrated in FIG. 3C, in the branch portion 16, the two second arm portions 40 and 42 (the second branch ports 40a and 42a) and the two third arm portions 46 and 48 (the third branch ports 46a and 48a) are point symmetrically provided with respect to the central line CL1 of the primary introduction portion 32a. That is, a space L1 between the central line CL1 of the primary introduction portion 32a and a central line CL2 of the second branch port 40a or 42a is approximately the same as a space L2 between the central line CL1 of the primary introduction portion 32a and a central line CL3 of the third branch port 46a or 48a. In other words, the central lines CL2 and CL3 are positioned on the same circumference.

In FIGS. 1 and 2, the branch tubes 18a to 18d are short tubes formed of a similar material to the primary tube 12. The plurality of branch tubes 18a to 18d is formed into the same size and the same shape as one another. In FIGS. 1 and 2, for convenience, the length of the branch tubes 18a and 18d and the length of the branch tubes 18b and 18c are illustrated in different lengths. However, in reality, the plurality of branch tubes 18a to 18d has an equal length.

The entire length of the branch tubes 18a to 18d is set to a length that enables joint of the branch tubes 18a to 18d with another tubes in an aseptic joining device after division of the medical preparation is completed and the branch tubes 18a to 18d are cut. To be specific, the entire length of the branch tubes 18a to 18d is 25 mm or more.

The plurality of division bags 20a to 20d is formed into a shape having the same size and the same shape as one another. The division bags 20a to 20d are formed in such a manner that sheet material made of a soft resin such as polyvinyl chloride or polyolefin and having flexibility is layered, and a seal portion in a peripheral edge of the sheet material is fusion-bonded (thermal fusion or high-frequency fusion) or glued, and formed into a bag shape.

The volume of each of the division bags 20a to 20d is set to 50 ml or more, for example. Note that the volume of the division bags 20a to 20d is smaller than the volume of the storage bag 100. The division bags 20a to 20d have inlets 21a to 21d to which the other end portions of the branch tubes 18a to 18d are provided.

The medical preparation dividing unit 10 further includes a holding tool 50 and a shape holding tool 52. The holding tool 50 holds the inlets 21a to 21d of the plurality of division bags 20a to 20d at the same height position above the branch portion 16. The shape holding tool 52 holds the other end side of the primary tube 12 in a curved shape.

The holding tool 50 includes a connection portion 54 and a mount portion 56. The connection portion 54 connects end portions of the plurality of division bags 20a to 20d on an opposite side of the inlets 21a to 21d with one another. The mount portion 56 is provided to the connection portion 54 and is detachably mountable to the primary tube 12. The connection portion 54 is formed of the resin material as the division bags 20a to 20d, for example. In the connection portion 54, a plurality of vulnerable portions 58 is formed so that the plurality of division bags 20a to 20d is separable from one another. The vulnerable portion 58 is formed in such a manner that a plurality of holes (perforation) is formed in the connection portion 54. Note that the vulnerable portion 58 is not limited thereto, and may have a thin-wall portion or a notch shape.

A fitting groove 60 into which the primary tube 12 is fittable is formed in the mount portion 56, for example. In this case, the mount portion 56 can be easily mounted to/dismounted from the primary tube 12, and blockage of a flow path of the primary tube 12 in a state where the mount portion 56 is mounted to the primary tube 12 can be suppressed.

The mount portion 56 is not limited to have the above configuration. The mount portion 56 may be formed of a tube-like member that can be tied to the primary tube 12 or may be a belt-like member having an adhesive surface peelably adhering to the primary tube 12. Further, the holding tool 50 is not limited to have the above configuration. The holding tool 50 may be a stand provided with a hook that can hang the plurality of division bags 20a to 20d at the same height position.

The shape holding tool 52 is used to hold the other end side of the primary tube 12 in an approximately U-shaped curved state, and is formed of a hard resin material into a rectangular shape in plan view. Two fitting grooves 62 and 64 into which the primary tube 12 is mounted extending along the overall width of the shape holding tool 52 are formed in the shape holding tool 52, for example. The fitting grooves 62 and 64 are similarly formed to the fitting groove 60 of the mount portion 56 in such a manner that the primary tube 12 is detachably mountable.

The fitting grooves 62 and 64 are separated in a longitudinal direction of the shape holding tool 52. A separation space between the fitting grooves 62 and 64 is set to a distance in which the other end side of the primary tube 12 can be curved at curvature by which the flow path of the primary tube 12 is not blocked.

The medical preparation dividing unit 10 according to the present embodiment is basically configured as described above. Next, a medical preparation dividing method of dividing the medical preparation in the storage bag 100 into the plurality of division bags 20a to 20d in an approximately uniform manner will be described. In the present embodiment, a holding process, a shape holding process, a connection process, a transfer process, a residual amount transfer process, and a separation process are performed in order.

As illustrated in FIG. 1, in the holding process, the fitting groove 60 of the holding tool 50 is mounted to the one end side of the primary tube 12. With the process, a curved portion 12a is formed on the other end side of the primary tube 12, and the plurality of division bags 20a to 20d are held with the inlets 21a to 21d facing downward at the same height.

At this time, the primary introduction portion 32a of the branch portion 16 is arranged above the curved portion 12a, and the second branch ports 40a and 42a and the third branch ports 46a and 48a of the branch portion 16 are arranged above the primary introduction portion 32a. Further, the plurality of division bags 20a to 20d takes the same posture such that an extending direction of the division bag goes along an up and down direction (gravity direction). In other words, the plurality of division bags 20a to 20d is held in the same posture with respect to a horizontal direction. A height H from a lowermost portion (a lower portion of the curved portion) of the primary tube 12 to the mount portion 56 mounted to the primary tube 12 is set to a dimension by which the branch tubes 18a to 18d are not bent.

In the holding process, an end portion of the U-shaped curved portion 12a on the other end side of the primary tube 12 is mounted to the fitting grooves 62 and 64 of the shape holding tool 52. With the process, the other end side of the primary tube 12 is reliably held in the curved shame. Note that the other end side of the primary tube 12 may be held in the curved shape in advance. In this case, the holding process may be provided.

Figure 4:
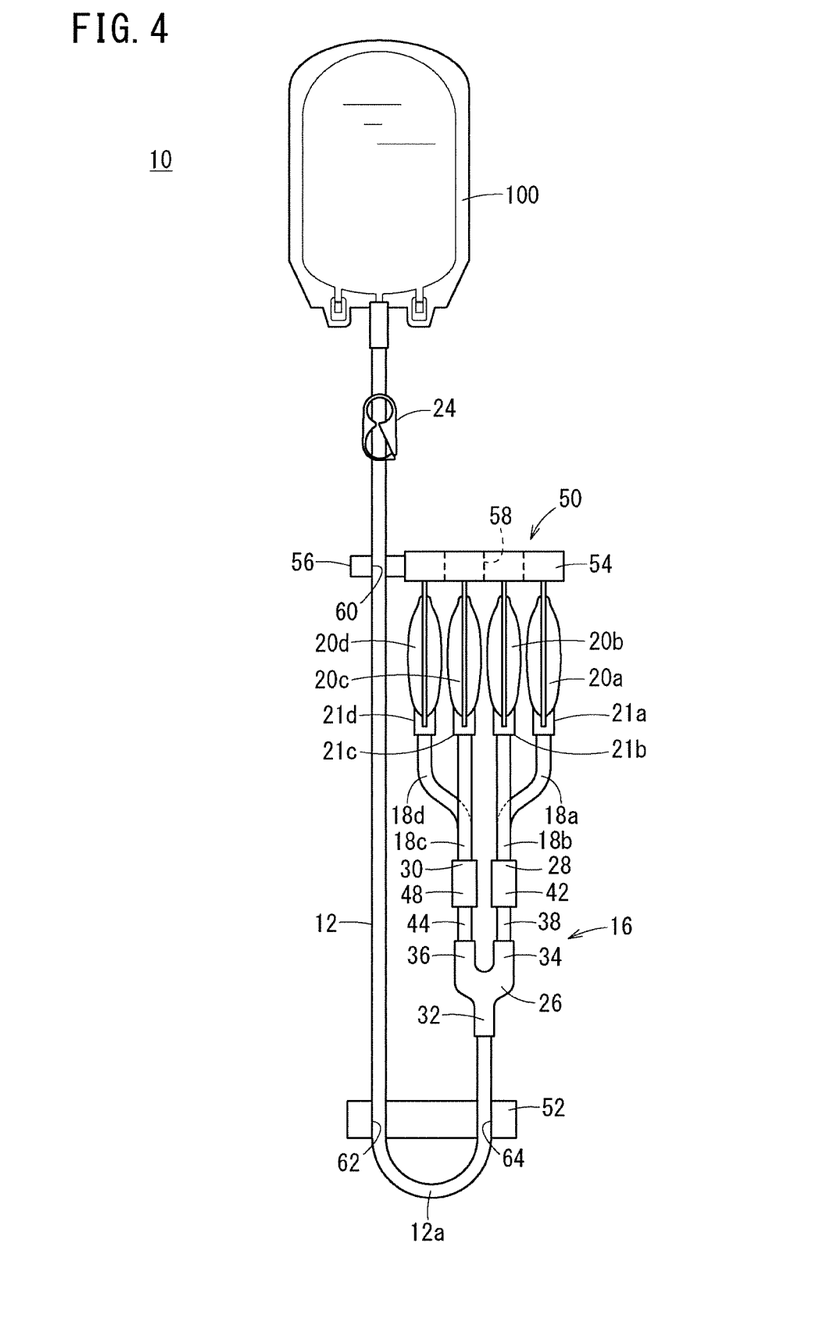
FIG. 4 is a schematic diagram illustrating a state in which a connection process and a holding process of a medical preparation dividing method according to an embodiment of the present invention are completed.

As illustrated in FIG. 4, in the connection process, the outlet of the storage bag 100 is joined with the one end of the primary tube 12 in an aseptic condition in a state where the clamp 24 is blocked. In the description below, the entire medical preparation dividing unit 10 provided with the storage bag 100 in place of the valve member 14 is also called "medical preparation dividing unit 10".

Figure 5:
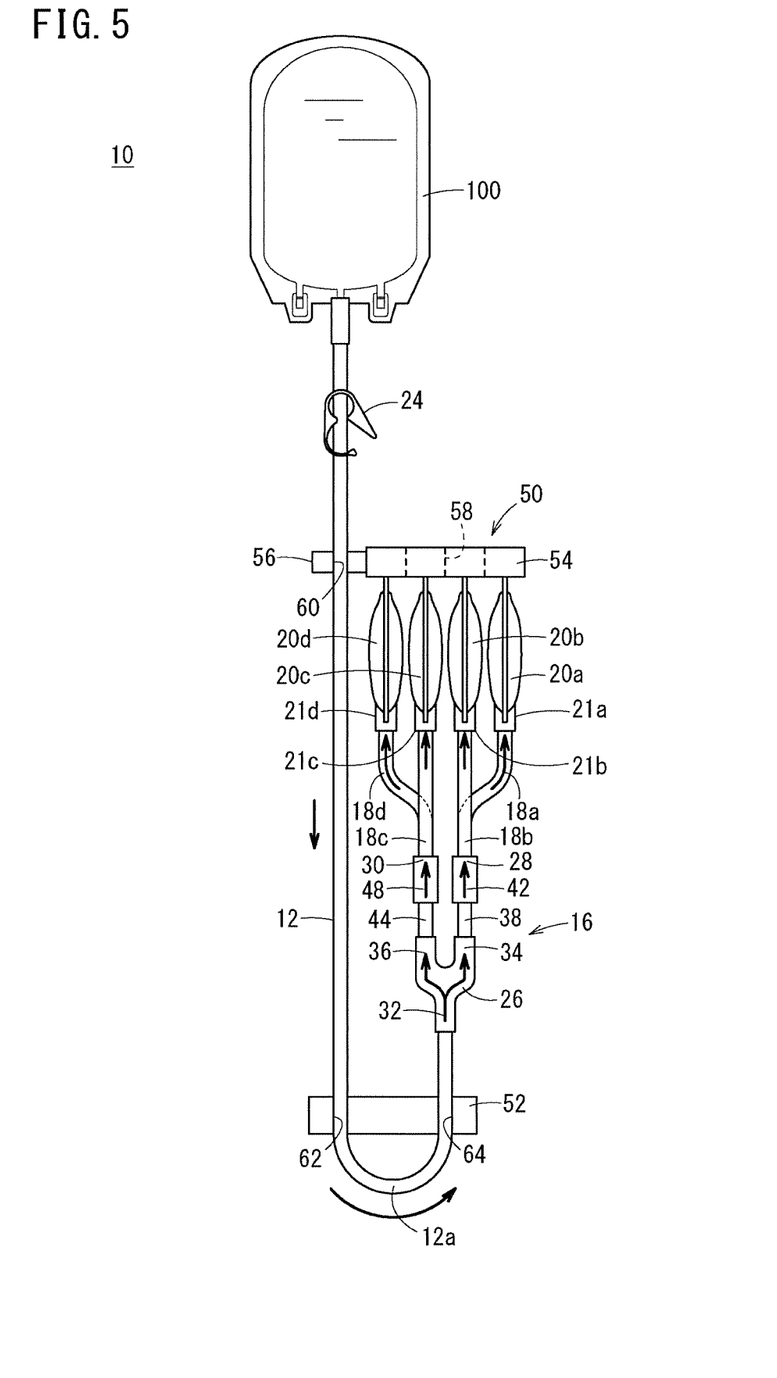
FIG. 5 is a schematic diagram illustrating the medical preparation dividing unit during a transfer process.

As illustrated in FIG. 5, in the transfer process, the clamp 24 is opened in the state where the storage bag 100 is arranged above the plurality of division bags 20a to 20d. At this time, the primary tube 12 extends from the one end to the curved portion 12a along the gravity direction. When the clamp 24 is opened, the medical preparation in the storage bag 100 flows by gravitational force in the primary tube 12, passes through the curved portion 12a, and flows into the primary introduction portion 32a of the branch portion 16. In the branch portion 16, the medical preparation introduced into the primary introduction portion 32a is transferred to the plurality of branch tubes 18a to 18d while pushing up the air in the branch portion 16.

Figure 6A:
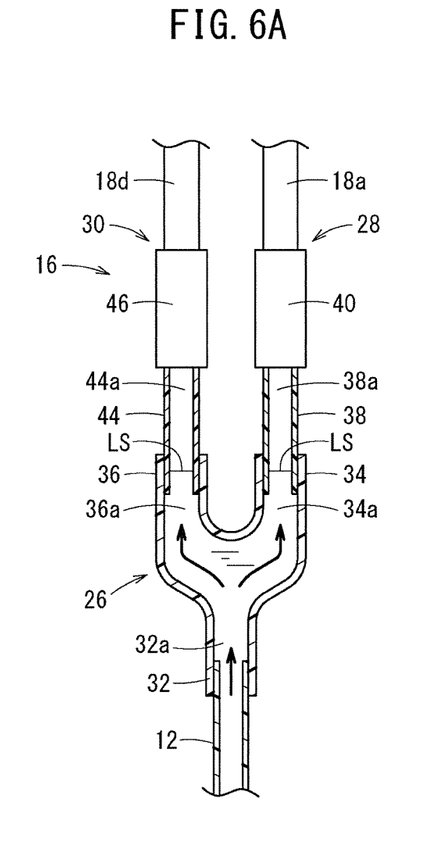
FIG. 6A is a sectional schematic diagram illustrating a state in which a medical preparation flows in a primary branch portion.

To be specific, as illustrated in FIG. 6A, the medical preparation introduced into the primary introduction portion 32a is divided and transferred to the two primary branch ports 34a and 36a in an approximately uniform manner. At this time, liquid levels LS of the medical preparation of the primary branch ports 34a and 36a are positioned at the same height. Then, the medical preparation flowing upward in the primary branch port 34a is introduced into the second introduction port 38a, and the medical preparation flowing upward in the primary branch port 36a is introduced into the third introduction port 44a.

Figure 6B:
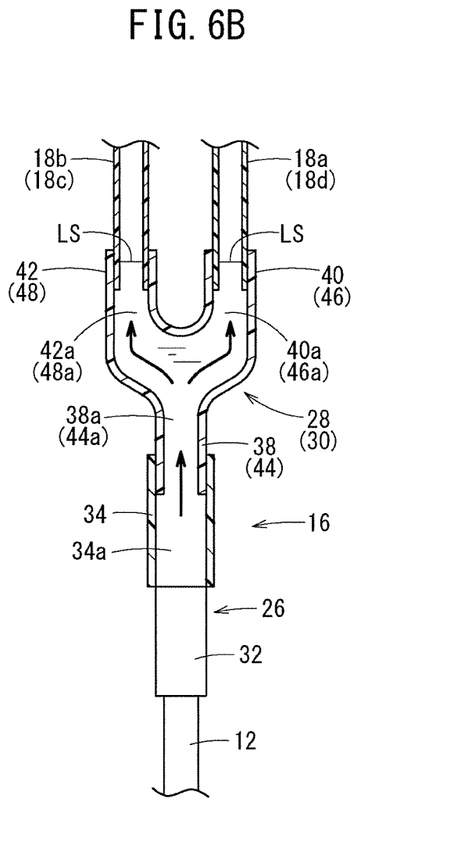
FIG. 6B is a sectional schematic diagram illustrating a state in which a medical preparation flows in a second branch portion.

Next, as illustrated in FIG. 6B, the medical preparation introduced into the second introduction port 38a is divided and transferred to the two second branch ports 40a and 42a in an approximately uniform manner, and the medical preparation introduced into the third introduction port 44a is divided and transferred to the two third branch ports 46a and 48a in an approximately uniform manner. At this time, liquid levels LS of the medical preparation of the second branch ports 40a and 42a and the third branch ports 46a and 48a are positioned at the same height.

After that, the medical preparation in the second branch port 40*a* is introduced into the branch tube 18*a*, the medical preparation in the second branch port 42*a* is introduced into the branch tube 18*b*, the medical preparation in the third branch port 46*a* is introduced into the branch tube 18*d*, and the medical preparation in the third branch port 48*a* is introduced into the branch tube 18*c* (see FIG. 5). At this time, liquid levels LS of the medical preparation of the branch tubes 18*a* to 18*d* are positioned at the same height. Then, the medical preparations in the branch tubes 18*a* to 18*d* flow upward and flow through the inlets 21*a* to 21*d* into the division bags 20*a* to 20*d*. That is, the medical preparation flowing by gravitational force in the primary tube 12 from the storage bag 100 changes the direction in the curved portion 12*a*, flows upward in the branch portion 16, and is approximately uniformly divided into the division bags 20*a* to 20*d* through the branch tubes 18*a* to 18*d*.

Figure 7:
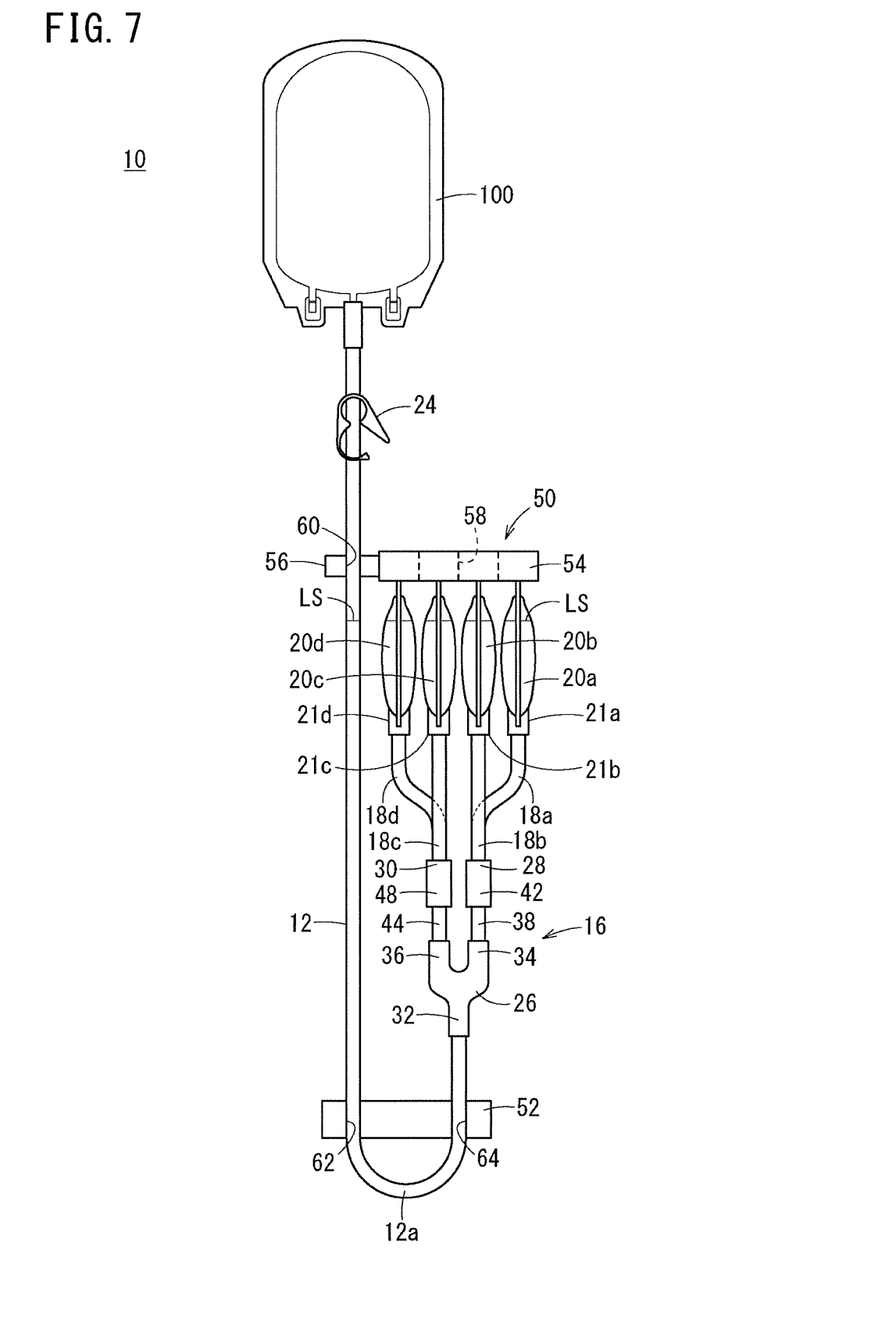
FIG. 7 is a schematic diagram illustrating a state in which the transfer process is completed.

Then, as illustrated in FIG. 7, the transfer of the medical preparation to the division bags 20*a* to 20*d* is stopped when the liquid level LS of the medical preparation in the primary tube 12 and the liquid levels LS of the medical preparation transferred to the division bags 20*a* to 20*d* are positioned at the same height. At this stage, the transfer process is terminated.

Figure 8:
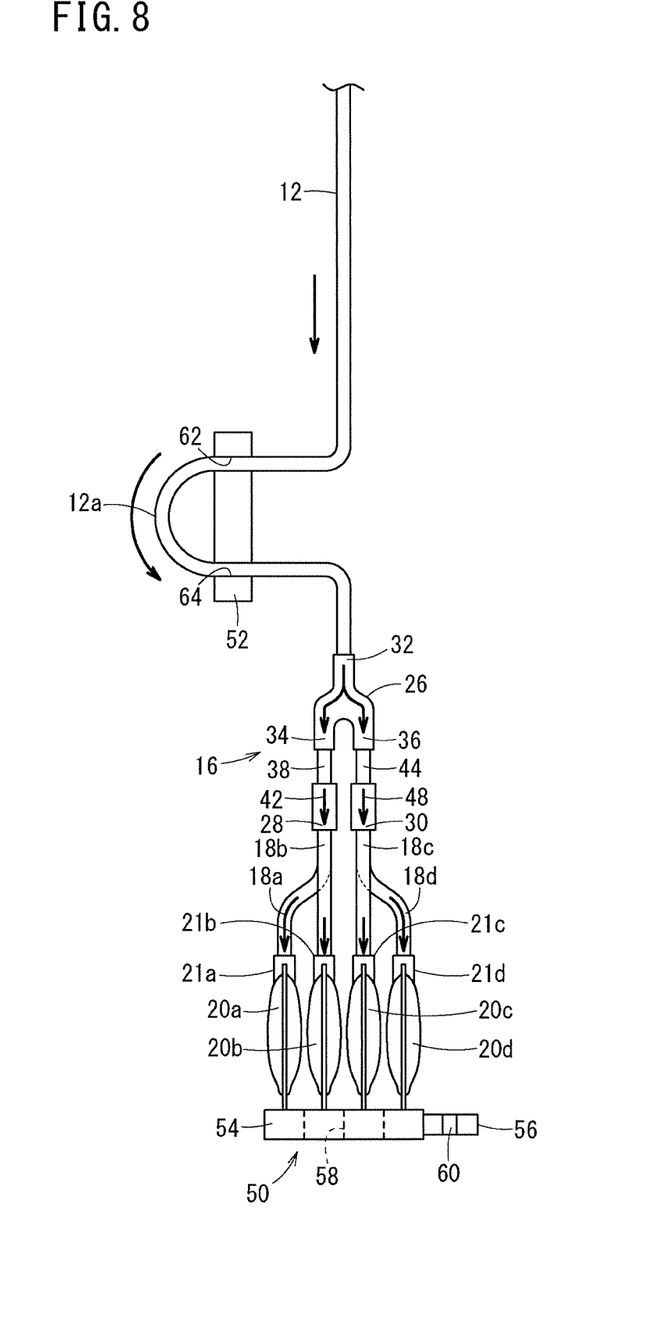
FIG. 8 is a schematic diagram illustrating the medical preparation dividing unit during a residual amount transfer process.

As illustrated in FIG. 8, in the residual amount transfer process, when the mount portion 56 of the holding tool 50 is detached from the primary tube 12, the branch portion 16 and the division bags 20*a* to 20*d* are arranged below the curved portion 12*a* in a vertically inverted state. At this time, the primary introduction portion 32*a* of the branch portion 16 is arranged below the curved portion 12*a*, and the second branch ports 40*a* and 42*a* and the third branch ports 46*a* and 48*a* of the branch portion 16 are arranged below the primary introduction portion 32*a*. Further, the plurality of division bags 20*a* to 20*d* are arranged with the inlets 21*a* to 21*d* facing upward at the same height position. With the arrangement, the medical preparation remaining in the primary tube 12 flows downward in the branch portion 16 and is transferred to the plurality of division bags 20*a* to 20*d* through the branch tubes 18*a* to 18*d*, and the total amount of the medical preparation stored in the storage bag 100 is divided into the division bags 20*a* to 20*d*.

Figure 9A:
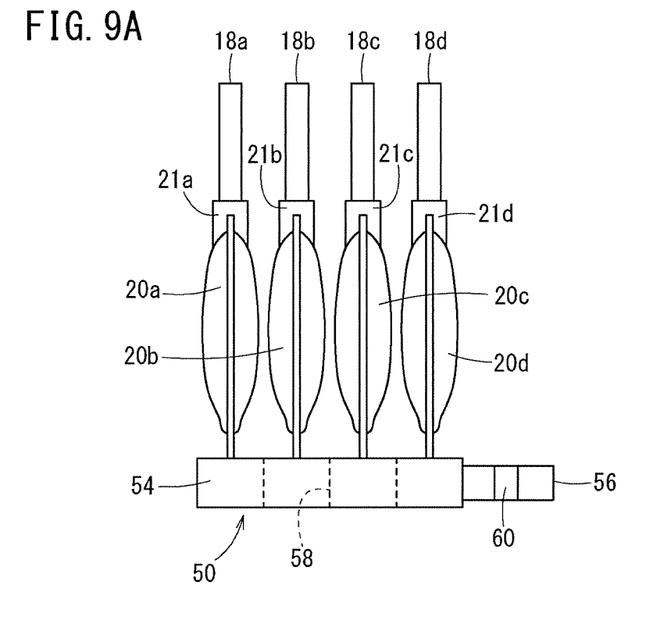
FIG. 9A is a primary explanatory diagram illustrating a separation process and FIG. 9B is a second explanatory diagram illustrating the separation process.
Figure 9B:
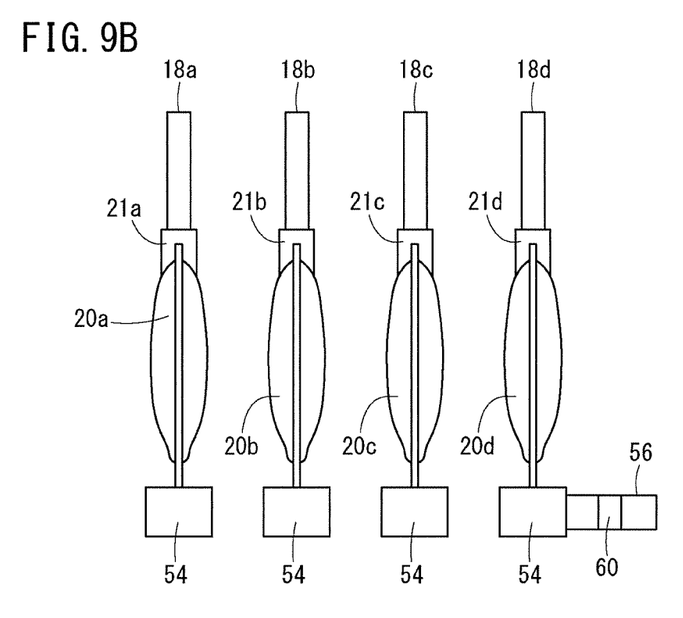

As illustrated in FIG. 9A, in the separation process, the branch tubes 18*a* to 18*d* are welded and sealed by a tube sealer or the like, and then the branch tubes 18*a* to 18*d* are cut in the sealed portions. Then, as illustrated in FIG. 9B, the plurality of division bags 20*a* to 20*d* is separated from one another by breaking the breakable portions 58 of the connection portion 54.

According to the present embodiment, when the medical preparation in the storage bag 100 is brought to flow by gravitational force in the primary tube 12 in the state where the plurality of division bags 20*a* to 20*d* is held with the holding tool 50, the medical preparation introduced from the primary tube 12 flows into the plurality of branch tubes 18*a* to 18*d* while pushing up the air in the branch portion 16. With the process, in the branch portion 16 and the branch tubes 18*a* to 18*d*, the medical preparation flows against gravitational force in an opposite direction to a proceeding direction. Therefore, flow separation in the branch portion 16 and the branch tubes 18*a* to 18*d* is suppressed, and influence of nonuniformity of a tube shape on the branch portion 16 and the branch tubes 18*a* to 18*d* can be reduced. Therefore, as a result, the medical preparation can be approximately uniformly transferred to the branch tubes 18*a* to 18*d*. Then, the medical preparations through the branch tubes 18*a* to 18*d* are approximately uniformly transferred to the plurality of division bags 20*a* to 20*d* having the inlets 21*a* to 21*d* having the same shape and the same size as one another and held at the same height. Therefore, the medical preparation in the storage bag 100 can be approximately uniformly divided into the plurality of division bags 20*a* to 20*d* by simple and easy work.

Further, the other end side of the primary tube 12 is held in the curved shape with the shape holding tool 52, and thus the medical preparation is introduced into the primary introduction portion 32*a* of the branch portion 16 from below. Therefore, the medical preparation in the branch portion 16 can be reliably brought to flow upward.

In the present embodiment, the lengths of the plurality of branch tubes 18*a* to 18*d* are approximately the same as one another, and flow path section areas of the plurality of branch tubes 18*a* to 18*d* are approximately the same as one another. In other words, the plurality of branch tubes 18*a* to 18*d* has approximately the same flow path volume. Therefore, the medical preparation can be further uniformly transferred to the plurality of division bags 20*a* to 20*d*.

Further, the central lines CL2 of the second branch ports 40*a* and 42*a* and the central lines CL3 of the third branch ports 46*a* and 48*a* are positioned on the same circumference around the central line CL1 of the primary introduction portion 32*a*. Therefore, the medical preparation introduced into the primary introduction portion 32*a* can be uniformly transferred to the branch tubes 18*a* to 18*d* through the second branch ports 40*a* and 42*a* and the third branch ports 46*a* and 48*a* with a simple configuration.

Further, the holding tool 50 includes the connection portion 54 that connects the plurality of division bags 20*a* to 20*d* with one another and the mount portion 56 provided to the connection portion 54 and detachably mountable to the primary tube 12. Therefore, the inlets 21*a* to 21*d* of the plurality of division bags 20*a* to 20*d* can be easily held at approximately the same height position by mounting the mount portion 56 to the primary tube 12.

Still further, the breakable portions 58 are formed in the connection portion 54. Therefore, the plurality of division bags 20*a* to 20*d* can be separated from one another by breaking the vulnerable portions 58 of the connection portion 54 after the medical preparation in the storage bag 100 is divided into the plurality of division bags 20*a* to 20*d*. With the process, the plurality of division bags 20*a* to 20*d* can be individually stored and used.

In the present embodiment, the medical preparation dividing unit 10 includes the clamp 24 that can block and open the primary tube 12. Therefore, the clamp 24 is opened after the plurality of division bags 20*a* to 20*d* is held with the holding tool 50, and the transfer process can be started.

In the present embodiment, the residual amount transfer process of causing the medical preparation in the primary tube 12 to flow downward to the division bags 20*a* to 20*d* through the branch portion 16 and the branch tubes 18*a* to 18*d* is performed by detaching the mount portion 56 from the primary tube 12 after the transfer process. Therefore, the total amount of the medical preparation in the storage bag 100 can be divided into the plurality of division bags 20*a* to 20*d*.

The medical preparation dividing unit 10 and the medical preparation dividing method according to the present embodiment are not limited to the above examples. The medical preparation dividing unit 10 may be provided with a bottle needle in place of the valve member 14. The breakable portions 58 may not be provided in the connection portion 54 of the holding tool 50. Further, in the medical preparation dividing method, the order to perform the holding process, the shape holding process, and the connection process can be arbitrarily changed.

The medical preparation dividing unit and the medical preparation dividing method according to the present invention are not limited to the above-described embodiments, and various configurations are employable without departing from the gist of the present invention.

What is claimed is:

1. A medical preparation dividing method of dividing a medical preparation stored in a storage member into a plurality of division bags, each division bag having an inlet, through a primary tube, a branch portion, and a plurality of branch tubes, the method comprising:
   connecting the storage member to a first end of the primary tube;
   holding, with a holding tool, the plurality of division bags with inlets facing downward, below the storage member and holding the inlets of the plurality of bags at the same height above the branch portion, the plurality of division bags being formed into the same shape and the same size as one another; and
   transferring the medical preparation to the plurality of division bags through the branch portion and the branch tubes, by flowing the medical preparation by gravitational force from the storage member to the primary tube after the holding step, wherein,
   the branch portion comprises a primary branch portion and a plurality of secondary branch portions, and
   in the transferring step,
      the medical preparation is transferred to the primary branch portion through a curved second end of the primary tube, flows upward in the primary branch portion, the primary branch portion dividing the medical preparation into at least first and second streams, and
      each of the streams is transferred to one of the secondary branch portions and flows upward in the respective secondary branch portion, the respective secondary branch portion dividing its stream into at least first and second divided streams, and
      each of the divided streams is transferred to one of the plurality of division bags through one of the plurality of branch tubes.

2. The medical preparation dividing method according to claim 1, wherein
   holding the second end of the primary tube in a curved shape with a shape holding tool is performed before the transfer process so that the medical preparation is introduced through the primary tube into the branch portion from below.

3. The medical preparation dividing method according to claim 2, further comprising
   causing a residual amount of the medical preparation in the primary tube to flow downward to the division bags through the branch portion and the branch tubes is performed, by canceling the holding of the plurality of division bags with the holding tool after the transferring step.

4. The medical preparation dividing method according to claim 3, wherein the holding tool includes a connection portion that connects the plurality of division bags with one another, and the dividing method further comprises
   separating the plurality of division bags from one another is performed by cutting the connection portion after the residual amount transfer process.

5. The medical preparation dividing method of claim 1 wherein the primary branch portion comprises a primary leg portion and two primary arm portions, the primary leg portion being connected to the primary tube and each of the primary arm portions being connected to one of said secondary branch portions, and the primary branch portion is line-symmetrically formed with respect to a central line of the primary leg portion as an axis of symmetry.

6. The medical preparation dividing method of claim 5 wherein each of the secondary branch portions comprises a secondary leg portion and two secondary arm portions, the secondary leg portion being connected to one of the primary arm portions of the primary branch portion and each of the secondary arm portions being connected to one of said division bags, and each secondary branch portion is line-symmetrically formed with respect to a central line of its respective secondary leg portion as an axis of symmetry.

* * * * *